(12) United States Patent
Shimazaki et al.

(10) Patent No.: US 10,969,372 B2
(45) Date of Patent: Apr. 6, 2021

(54) GAS SENSOR

(71) Applicant: NGK SPARK PLUG CO., LTD, Nagoya (JP)

(72) Inventors: Yuji Shimazaki, Nagoya (JP); Hironari Furuta, Nagoya (JP); Kentaro Mori, Nagoya (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 154 days.

(21) Appl. No.: 16/214,344

(22) Filed: Dec. 10, 2018

(65) Prior Publication Data

US 2019/0178861 A1   Jun. 13, 2019

(30) Foreign Application Priority Data

Dec. 11, 2017  (JP) .............................. JP2017-236690
Dec. 11, 2017  (JP) .............................. JP2017-237183
Aug. 10, 2018  (JP) .............................. JP2018-151552

(51) Int. Cl.
*G01N 33/00*    (2006.01)

(52) U.S. Cl.
CPC ..... *G01N 33/0009* (2013.01); *G01N 33/0036* (2013.01)

(58) Field of Classification Search
CPC ....................... G01N 33/0009; G01N 33/0036
See application file for complete search history.

(56) References Cited

U.S. PATENT DOCUMENTS

| | | | | |
|---|---|---|---|---|
| 4,578,174 A * | 3/1986 | Kato | .................. | G01N 27/4067 204/427 |
| 4,756,885 A * | 7/1988 | Raff | ................... | G01N 27/4077 204/428 |
| 5,795,454 A * | 8/1998 | Friese | .................. | G01N 27/407 204/424 |
| 5,874,664 A * | 2/1999 | Watanabe | ............ | G01N 27/407 73/23.32 |
| 6,015,533 A * | 1/2000 | Young | ................ | G01N 33/0009 204/428 |
| 6,214,186 B1 * | 4/2001 | Watanabe | .......... | G01N 27/4077 204/427 |
| 6,222,372 B1 * | 4/2001 | Fukaya | ................ | G01N 27/407 204/424 |

(Continued)

FOREIGN PATENT DOCUMENTS

JP           3932881 B2    6/2007

*Primary Examiner* — Jamel E Williams
(74) *Attorney, Agent, or Firm* — Stites & Harbison, PLLC; Jeffrey A. Haeberlin; James R. Hayne

(57) ABSTRACT

A gas sensor includes a sensing element, a metal shell that is tubular and that surrounds the sensing element, and a protector made of a metal and fixed to the metal shell. A back end portion of the protector is joined to an outer surface of the metal shell to form a joined portion. A coefficient of thermal expansion of a material of the protector at 800 degrees Celsius is higher than a coefficient of thermal expansion of a material of the metal shell at 800 degrees Celsius. In a cross section of a portion of the gas sensor including the joined portion, a minimum distance t1 between the outer surface of the metal shell and an outer surface of the protector and a minimum distance t2 between the outer surface of the metal shell and an inner surface of the metal shell satisfy $0.6 \leq (t1/t2) \leq 2.0$.

5 Claims, 3 Drawing Sheets

(56) References Cited

U.S. PATENT DOCUMENTS

| | | | | |
|---|---|---|---|---|
| 6,548,023 | B1* | 4/2003 | Matsuo | G01N 27/407 422/83 |
| 7,036,352 | B2* | 5/2006 | Isomura | G01N 27/4077 73/23.2 |
| 7,927,475 | B2* | 4/2011 | Isomura | G01N 27/4077 204/428 |
| 2004/0245482 | A1* | 12/2004 | Sato | G01N 27/4071 250/493.1 |
| 2008/0223110 | A1* | 9/2008 | Weyl | G01N 27/4077 73/31.05 |
| 2009/0173630 | A1* | 7/2009 | Mori | G01N 27/407 204/424 |
| 2011/0209523 | A1* | 9/2011 | Otsubo | G01N 27/4077 73/23.31 |
| 2013/0032480 | A1* | 2/2013 | Ito | G01N 27/419 204/424 |
| 2016/0223369 | A1* | 8/2016 | Mori | G01N 27/4077 |
| 2017/0212090 | A1* | 7/2017 | Kume | G01N 33/0009 |

* cited by examiner

| RATIO (t1/t2) | 0.5 | 0.6 | 0.8 | 1.2 | 2.5 |
|---|---|---|---|---|---|
| SEPARATION OF BACK-END COUPLED PORTION | BAD | GOOD | GOOD | GOOD | GOOD |
| DEFORMATION OF METAL SHELL | GOOD | GOOD | GOOD | GOOD | BAD |

GAS SENSOR

CROSS REFERENCE TO RELATED APPLICATION

The present application claims priority to Japanese Patent Application No. 2017-236690, which was filed on Dec. 11, 2017, the disclosure of which is herein incorporated by reference in its entirety.

BACKGROUND OF THE INVENTION

1. Field of the Invention

The present invention relates to a gas sensor including a sensing element that is exposed to gas to be detected and that detects a specific gas component contained in the gas.

2. Description of the Related Art

Examples of known gas sensors used to increase the fuel efficiency or perform combustion control of an internal combustion engine, such as an automobile engine, include oxygen sensors that detect the oxygen concentration in exhaust gas and air/fuel ratio sensors.

An example of such a gas sensor includes a sensing element including a detecting portion, which detects the concentration of specific gas, at the front end thereof; a metal shell that holds the sensing element; and a metal protector that covers the detecting portion, which protrudes from the front end of the metal shell, to protect the detecting portion (see, for example, PTL 1).

This type of gas sensor is subjected to heating-cooling cycles in which the gas sensor is exposed to high-temperature exhaust gas so that, in particular, a welded portion between the protector and the metal shell at the front end of the gas sensor is heated to a high temperature, and is then cooled. Accordingly, there is a risk that the welded portion will break due to stress repeatedly applied thereto during the heating-cooling cycles. To prevent this, the gas sensor according to PTL 1 is configured such that the protector and the metal shell have a small difference in coefficient of thermal expansion to reduce the repeated stress and thereby reduce the occurrence of breakage of the welded portion.

PATENT LITERATURE

PTL 1 is Japanese Patent No. 3932881 (FIG. 1)

In recent years, automobile components having higher heat resistant temperatures have been desired, and it has become necessary to change the materials of the components to those having higher heat resistances. In particular, heat resistance requirements on the protector, which is positioned outermost at the front end of the gas sensor, are most severe. Although the material of the protector may be changed to a heat-resistant material (Inconel (registered trademark) alloy) to meet the requirements, such a material is expensive.

The protector may instead be made of an inexpensive heat resistant material, such as an austenitic stainless steel to which Nb is added. However, this material has a coefficient of thermal expansion higher than that of the metal shell (for example, SUS430), and is therefore disadvantageous in that the protector expands more than the metal shell does when the above-described repeated stress is applied, which increases the risk of breakage of the welded portion.

SUMMARY OF THE INVENTION

The present invention has been made in light of the above-described circumstances, and an object of the present invention is to provide a gas sensor in which breakage or other damage to a joined portion between a protector and a metal shell does not easily occur even when the coefficient of thermal expansion of the material of the protector is higher than that of the material of the metal shell.

A gas sensor according to the present invention includes a sensing element that extends in an axial line direction and includes a detecting portion at a front end of the sensing element; a metal shell that is tubular and made of a metal, the metal shell surrounding the sensing element such that the detecting portion projects from a front end of the metal shell; and a protector made of a metal, the protector containing the detecting portion and being fixed to the metal shell. A back end portion of the protector is joined to an outer surface of the metal shell to form a joined portion. A coefficient of thermal expansion of a material of the protector at 800 degrees Celsius is higher than a coefficient of thermal expansion of a material of the metal shell at 800 degrees Celsius. In a cross section of a portion of the gas sensor including the joined portion, a minimum distance t1 between the outer surface of the metal shell and an outer surface of the protector and a minimum distance t2 between the outer surface of the metal shell and an inner surface of the metal shell satisfy $0.6 \leq (t1/t2) \leq 2.0$. In other words, a back end portion of the protector is joined to an outer surface of the metal shell to form a joined portion having a cross section in which a minimum distance t1 between the outer surface of the metal shell and an outer surface of the protector and a minimum distance t2 between the outer surface of the metal shell and an inner surface of the metal shell satisfy $0.6 \leq (t1/t2) \leq 2.0$.

The gas sensor, in which the coefficient of thermal expansion of the material of the protector at 800 degrees Celsius is higher than that of the material of the metal shell at 800 degrees Celsius, may be repeatedly heated and cooled in heating-cooling cycles. Even in such a case, the strength of the back end portion of the protector and the strength of the metal shell in the joined portion are appropriately balanced across the point at which the ratio (t1/t2) is 1, so that the repeated stress and deformation of the metal shell can be reduced. Thus, the risk of breakage or other damage to the joined portion can be reduced.

When the ratio (t1/t2) is less than 0.6, the thickness of the back end portion is small relative to the thickness of the metal shell. Accordingly, the strength of the back end portion decreases and the repeated stress increases. When the ratio (t1/t2) is above 2.0, the thickness of the metal shell is small relative to the thickness of the back end portion. Accordingly, the strength of the metal shell decreases and deformation of the metal shell increases. As a result, the risk of breakage or other damage to the joined portion significantly increases.

The protector may include an inner protector element arranged such that a gap is provided (defined) between the inner protector element and the detecting portion, and an outer protector element arranged such that a gap is provided (defined) between the outer protector element and the inner protector element. The joined portion is formed on a back-end coupled portion in which a back end portion of the inner protector element and a back end portion of the outer protector element overlap.

Thus, the present invention is applicable not only to a gas sensor in which the protector has a one-element structure but also to a gas sensor in which the protector has a two-element structure including an inner protector element and an outer protector element.

In the gas sensor according to the present invention, the metal shell may include a first inner surface in a region obtained by projecting the joined portion on the outer surface of the metal shell onto the inner surface of the metal shell, the first inner surface being radially outside a back inner surface of the metal shell, the back inner surface being connected to a back end of the first inner surface. In other words, the metal shell includes a first inner surface in a region obtained by projecting the joined portion on the outer surface of the metal shell onto the inner surface of the metal shell and a back inner surface connected to a back end of the first inner surface, the first inner surface being radially outside the back inner surface.

According to this gas sensor, the space around the detecting portion of the sensing element surrounded by the entire inner surface of the metal shell is larger than that in the case where the first inner surface, which have the joined portion disposed outside thereof, and the back inner surface of the metal shell are flush with each other in the axial line direction. Accordingly, gas to be detected more easily flows to and from the detecting portion, and the detection precision increases. In addition, the protector may have a greater diameter (be farther away from the detecting portion) than in the case where the first inner surface, which have the joined portion disposed outside thereof, and the back inner surface of the metal shell are flush with each other in the axial line direction. Accordingly, the risk of entrance of water from the outer surface of the protector (outer protector element) toward the sensing element can be reduced.

In the gas sensor according to the present invention, a tensile strength of a material of the protector according to JIS-G0567 at 800 degrees Celsius may be greater than a tensile strength of a material of the metal shell according to JIS-G0567 at 800 degrees Celsius.

According to this gas sensor, the heat resistance of the protector, which is positioned outermost at the front end of the gas sensor, is further increased. As a result, the heat resistance of the gas sensor can be further increased.

In the gas sensor according to the present invention, a material of the protector may be an austenitic stainless steel and a material of the metal shell may be a ferritic stainless steel.

According to this gas sensor, the overall heat resistance of the gas sensor can be increased by using an inexpensive material, and the risk of breakage or other damage to the joined portion can be reduced.

The present invention provides a gas sensor in which breakage or other damage to a joined portion between a protector and a metal shell does not easily occur even when the coefficient of thermal expansion of the material of the protector is higher than that of the material of the metal shell.

BRIEF DESCRIPTION OF THE DRAWINGS

Illustrative aspects of the invention will be described in detail with reference to the following figures wherein.

DESCRIPTION OF THE PREFERRED EMBODIMENTS

An embodiment of the present invention will now be described.

Figure 1:
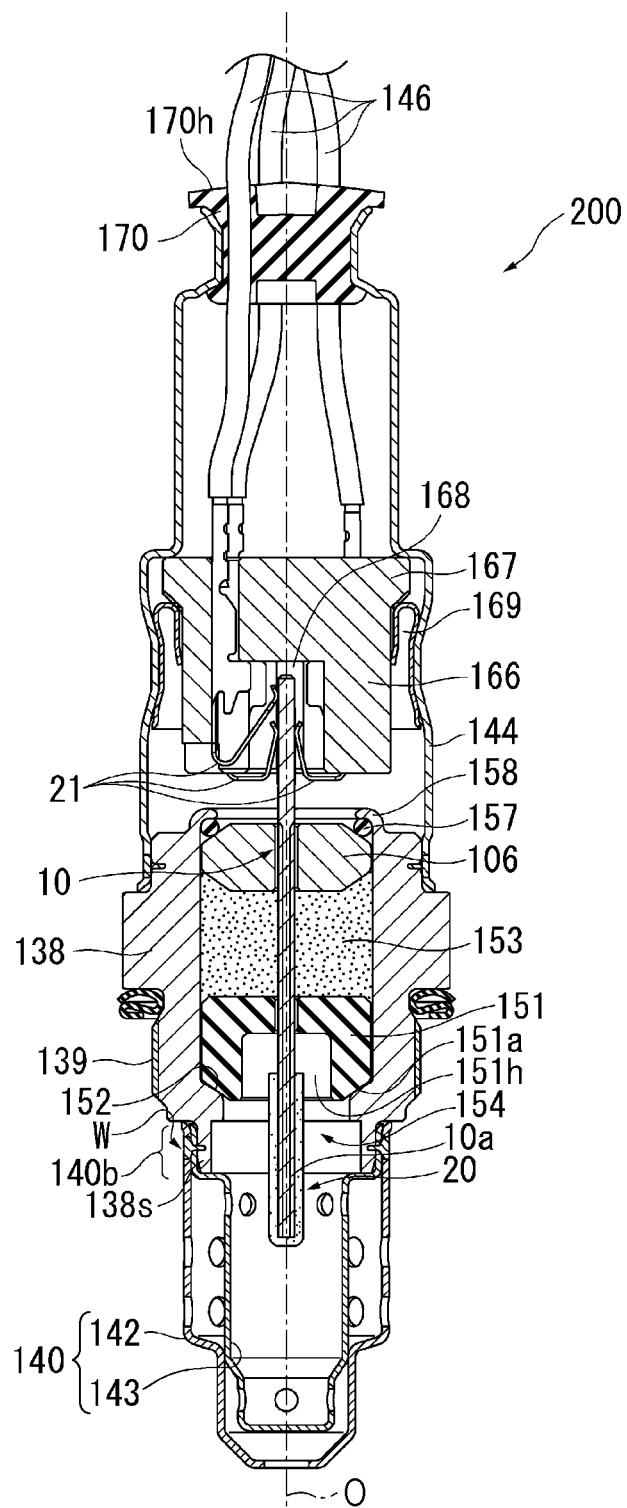
FIG. 1 is a sectional view of a gas sensor according to an embodiment of the present invention taken in the longitudinal direction.
Figure 2:
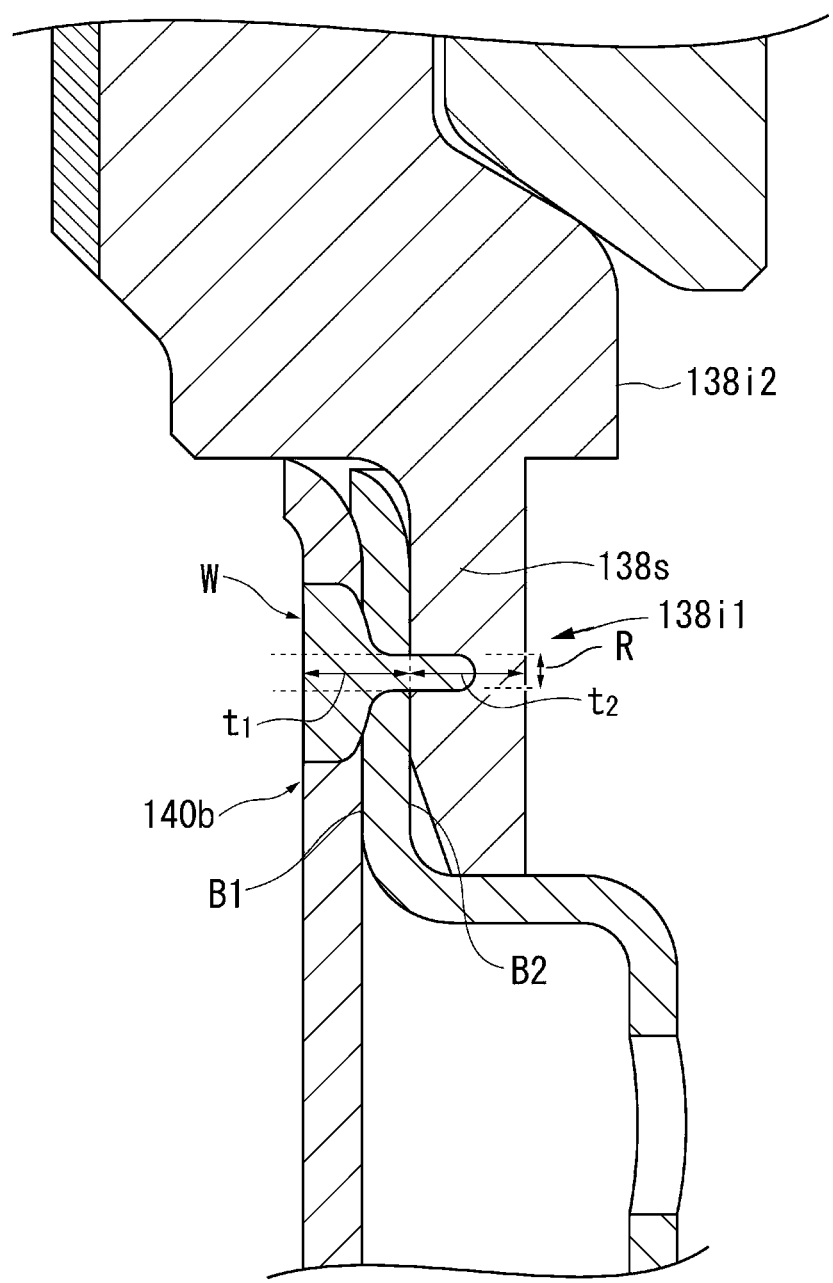
FIG. 2 is a partial enlarged view of FIG. 1, illustrating the region around a joined portion.

FIG. 1 is an overall sectional view of a gas sensor (oxygen sensor) 200 according to the embodiment of the present invention taken in the longitudinal direction. FIG. 2 is a partial enlarged view of FIG. 1 illustrating the region around a joined portion.

The gas sensor 200 is an oxygen sensor (universal A/F heated exhaust gas oxygen (UEGO) sensor) that detects the oxygen concentration in exhaust gas of automobiles or various internal combustion engines.

The gas sensor 200 includes a protector 140 (described below) having a two-element structure including an inner protector element 143 and an outer protector element 142.

The gas sensor 200 illustrated in FIG. 1 includes a tubular metal shell 138, a plate-shaped sensing element 10, a tubular ceramic sleeve 106, a ceramic holder 151, a ceramic separator 166, five metal terminals 21 (of which only three are illustrated in FIG. 1), and the protector 140 having the two-element structure. The metal shell 138 includes a threaded portion 139 on the outer surface thereof. The threaded portion 139 is used to fix the gas sensor 200 to an exhaust pipe. The sensing element 10 extends in the direction of an axial line O (longitudinal direction of the gas sensor 200: vertical direction in FIG. 1). The ceramic sleeve 106 circumferentially surrounds a back portion of the sensing element 10. The separator 166 is arranged to surround the back end portion of the sensing element 10 disposed in a front portion of an insertion hole 168 that extends through the separator 166 in the axial line direction. The metal terminals 21 are disposed between the sensing element 10 and the separator 166. The protector 140 is fixed to a front portion of the metal shell 138.

The sensing element 10 includes a detecting portion 10a at the front end thereof. The detecting portion 10a is covered by a porous protecting layer 20 made of, for example, alumina.

The metal shell 138, which is made of stainless steel, has a through hole 154 that extends therethrough in the axial line direction, and has a substantially tubular shape including a ledge portion 152 that projects radially inward in the through hole 154. The sensing element 10 is placed in the through hole 154 so that a front portion of the sensing element 10 including the detecting portion 10a projects from the front end of the through hole 154. The ledge portion 152 has an inner tapered surface that is inclined with respect to a plane perpendicular to the axial line direction.

The ceramic holder 151, which has an annular shape and is made of alumina, a powder filler layer 153 (hereinafter referred to also as a talc ring 153), and the above-described ceramic sleeve 106 are arranged in that order in the front-to-back direction so as to circumferentially surround the sensing element 10 in the through hole 154 in the metal shell 138.

A crimp packing 157 is disposed between the ceramic sleeve 106 and a back end portion 158 of the metal shell 138. The back end portion 158 of the metal shell 138 is crimped so that the crimp packing 157 presses the ceramic sleeve 106 forward.

The ceramic holder 151, which is made of an insulating ceramic (for example, alumina), has a short, substantially cylindrical shape and includes a forward facing surface 151a that is tapered toward the front end thereof. The ceramic holder 151 is pressed by the talc ring 153 at the back end thereof while an outer peripheral portion of the forward facing surface 151a is retained by the ledge portion 152 of the metal shell 138, and is thereby positioned in the metal shell 138 and fitted to the metal shell 138 with a clearance therebetween.

The ceramic holder 151 has a recess 151h at the front end thereof. The recess 151h surrounds an insertion hole for the sensing element 10 and is recessed toward the back end of the ceramic holder 151.

As illustrated in FIG. 1, the protector 140, which has a tubular two-element structure and is made of a metal, is attached to the outer periphery of a front end portion 138s (bottom portion in FIG. 1) of the metal shell 138 by, for example, welding. The protector 140 has a plurality of holes and covers the front end portion (portion including the detecting portion 10a) of the sensing element 10 that projects from the metal shell 138.

The protector 140 having the two-element structure includes the inner protector element 143, which has a tubular shape with a bottom and surrounds the detecting portion 10a with a gap therebetween, and the outer protector element 142, which also has a tubular shape with a bottom and surrounds the inner protector element 143 with a gap therebetween. Back end portions of the inner protector element 143 and the outer protector element 142 at the open ends thereof are joined together to form a back-end coupled portion 140b.

The back-end coupled portion 140b is joined to the outer surface of the front end portion 138s of the metal shell 138 by welding (all around welding in this embodiment) to form a joined portion W.

A shell 144 is fixed to the outer periphery of a back portion of the metal shell 138. A grommet (sealing member) 170 made of rubber is fitted to the opening at the back end (top end in FIG. 1) of the shell 144. The grommet 170 has lead-wire insertion holes 170h through which five lead wires 146 (of which only three are illustrated in FIG. 1) extend. The five lead wires 146 are individually electrically connected to the five metal terminals 21 (of which only three are illustrated in FIG. 1) of the sensing element 10.

The separator 166 is disposed apart from the metal shell 138 at the back end (top end in FIG. 1) of the sensing element 10, which projects from the back end portion 158 of the metal shell 138. The separator 166 is disposed around a total of five electrode pads (not shown) formed on the back principal surface of the sensing element 10. The separator 166 is tubular and has the insertion hole 168 that extends therethrough in the axial line direction. The separator 166 also includes a flange portion 167 that projects radially outward from the outer surface thereof. The separator 166 is arranged so that the flange portion 167 is in contact with a step portion of the shell 144, and is secured in the shell 144 by crimping the shell 144 with a holding member 169 disposed therebetween.

FIG. 2 is a partial enlarged view of FIG. 1, illustrating the region around the joined portion W. The joined portion W is a portion in which the outer surface of the front end portion 138s of the metal shell 138 is not simply in contact with the back-end coupled portion 140b but is a portion in which the outer surface of the front end portion 138s of the metal shell 138 and the back-end coupled portion 140b are integrated together. More specifically, in the enlarged sectional view of a portion in which the outer surface of the metal shell 138 is in contact with the back-end coupled portion 140b taken in the direction of the axial line O, the joined portion W is a portion P having no boundary line B1 between the inner protector element 143 and the outer protector element 142 and no boundary line B2 between the inner protector element 143 and the front end portion 138s of the metal shell 138. This is because portions in which the materials of the inner protector element 143, the outer protector element 142, and the metal shell 138 are not integrated together individually expand when heated, and are therefore hardly subjected to repeated stress.

In the cross section of a portion including the joined portion W, t1 denotes the minimum distance between the outer surface of the metal shell 138 and the outer surface of the protector 140, and t2 denotes the minimum distance between the outer surface of the metal shell 138 and the inner surface of the metal shell 138.

When the protector 140 has a two-element structure, the outer surface thereof is the outermost surface of the protector 140, that is, the outer surface of the outer protector element 142.

The distances t1 and t2 are determined with reference to a cross section of a portion including the joined portion W. Therefore, t2 is determined by the inner and outer surfaces of the front end portion 138s of the metal shell 138 in the joined portion W.

Since the back-end coupled portion 140b and the metal shell 138 are integrated together in the joined portion W, the boundary therebetween is assumed to be an imaginary straight line that coincides with the boundary line B2 in the regions in front of and behind the joined portion W. Therefore, the distance t2 is the distance between the inner surface of the metal shell 138 and the above-described imaginary straight line in the joined portion W. The distance t1 is the distance between the outer surface of the back-end coupled portion 140b and the above-described imaginary straight line in the joined portion W.

According to the present invention, the coefficient of thermal expansion of the material of the protector 140 (the inner protector element 143 and the outer protector element 142) at 800 degrees Celsius is higher than that of the material of the metal shell 138 at 800 degrees Celsius. For example, in this embodiment, the protector 140 is made of an austenitic stainless steel to which Nb is added, and the metal shell 138 is made of SUS430LX according to Japanese Industrial Standard (JIS), which is a ferritic stainless steel.

When the gas sensor 200 is subjected to repeated stress by being exposed to, for example, high-temperature exhaust gas and then cooled, the protector 140, which is at the outermost position at the front end of the gas sensor 200, expands more than the metal shell 138 does. This increases the risk of breakage or other damage of the welded portion (joined portion W), as described above.

Accordingly, in the present invention, $0.6 \leq (t1/t2) \leq 2.0$ is satisfied to reduce the risk of breakage or other damage of the joined portion W between the protector 140 and the metal shell 138. In addition, the protector 140 is made of an inexpensive heat resistant material whose coefficient of thermal expansion at 800 degrees Celsius is higher than that of the metal shell at 800 degrees Celsius. Thus, the overall heat resistance of the gas sensor 200 can be increased.

The reason why the risk of breakage or other damage to the joined portion W can be reduced by controlling the ratio (t1/t2) will now be described with reference to FIG. 3.

Figures 3, 4:
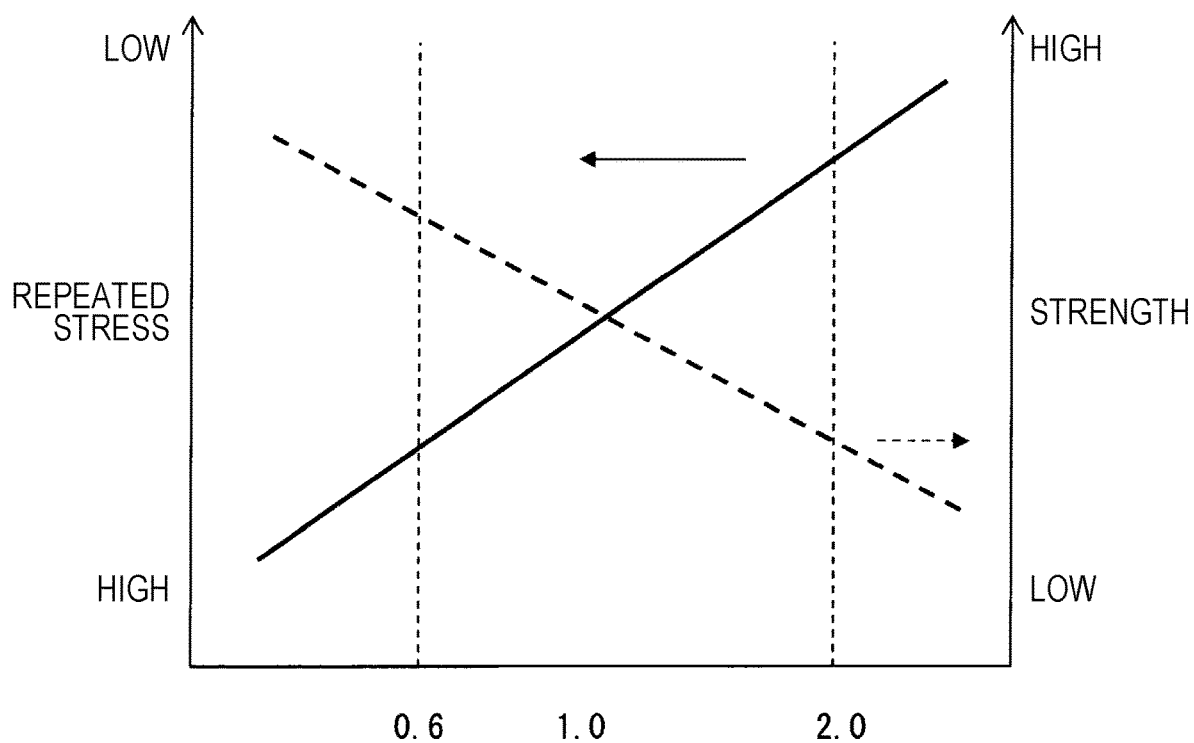
FIG. 3 is a graph showing the influence of the ratio (t1/t2) between the distances defined by a back-end coupled portion and a metal shell in the joined portion on various characteristics.
FIG. 4 is a table showing the results of evaluation regarding breakage or other damage to the joined portion when the ratio (t1/t2) between the distances defined by the back-end coupled portion and the metal shell in the joined portion is changed.

FIG. 3 is a graph showing the influence of the ratio (t1/t2) between the distances defined by the back-end coupled portion 140b and the front end portion 138s of the metal shell 138 in the joined portion W on various characteristics.

According to the present invention, it is assumed that t2 is smaller than that in a metal shell according to the related art, and is about 1.7 times t1 ((t1/t2)=0.6) at a maximum. Thus, the influence of the repeated stress can be controlled by changing the ratio between t2 and t1. In contrast, in the structure of the related art, in which t2 is significantly greater than t1 (for example, (t1/t2) is 0.2 or less), deformation of the metal shell hardly changes when (t1/t2) is changed. Accordingly, it is difficult to control the influence of the repeated stress.

As shown by the solid line in FIG. 3, in the range around the point at which ratio (t1/t2)=1, the distance t1, that is, the thickness of the back-end coupled portion 140b increases as the ratio increases. Accordingly, the strength of the back-end coupled portion 140b increases and approaches the strength of the front end portion 138s of the metal shell 138. Therefore, the repeated stress applied to the joined portion W in the heating-cooling cycle is reduced, and the risk of breakage or other damage to the joined portion W is reduced accordingly. Thus, as far as the back-end coupled portion 140b is concerned, the ratio is preferably as high as possible.

As the ratio increases, the distance t2, that is, the thickness of the front end portion 138s of the metal shell 138, decreases. Accordingly, as shown by the broken line in FIG. 3, the strength of the front end portion 138s of the metal shell 138 decreases, and the amount of deformation of the metal shell 138 due to the repeated stress increases. As a result, the risk of breakage or other damage to the joined portion W increases. Therefore, as far as the metal shell 138 is concerned, the ratio is preferably as low as possible.

This shows that the ratio (t1/t2) has an appropriate range around 1. The appropriate range for the ratio was determined by experiments described below.

When the ratio (t1/t2) is less than 0.6, the thickness of the back-end coupled portion 140b is small relative to the thickness of the metal shell 138 in the joined portion W. Accordingly, the strength of the back-end coupled portion 140b decreases and the repeated stress increases. As a result, the risk of breakage or other damage to the joined portion W significantly increases.

When the ratio (t1/t2) is above 2.0, the thickness of the metal shell 138 is small relative to the thickness of the back-end coupled portion 140b in the joined portion W. Accordingly, the strength of the metal shell 138 decreases and deformation of the metal shell 138 increases. As a result, the risk of breakage or other damage to the joined portion W significantly increases.

The ratio (t1/t2) is preferably in the range of 0.6 to 1.6, more preferably 0.8 to 1.6. Also, the ratio (t1/t2) is preferably in the range of 0.6 to 1.5, more preferably 0.8 to 1.5. Also, the ratio (t1/t2) is preferably in the range of 0.6 to 1.3, more preferably 0.8 to 1.3.

Referring to FIG. 2, in the present invention, region R is defined as a projection region obtained by projecting the joined portion W on the outer surface of the metal shell onto the inner surface of the metal shell 138 in a radially inward direction. The inner surface of the front end portion 138s of the metal shell 138 in the region R is defined as a first inner surface 138i1. The first inner surface 138i1 is radially outside a back inner surface 138i2 of the metal shell 138. The back inner surface 138i2 is connected to the back end of the first inner surface 138i1.

In this case, the space around the detecting portion 10a of the sensing element 10 surrounded by the inner surface of the metal shell 138 is larger than that in the case where the first inner surface 138i1 and the back inner surface 138i2 are flush with each other in the direction of the axial line O. Accordingly, gas to be detected more easily flows to and from the detecting portion 10a, and the detection precision increases. In addition, the protector 140 may have a greater diameter (be farther away from the detecting portion 10a) than in the case where the first inner surface 138i1 and the back inner surface 138i2 are flush with each other in the direction of the axial line O. Accordingly, the risk of entrance of water from the outer surface of the protector 140 (outer protector element 142) toward the sensing element 10 can be reduced.

The inner surface of the metal shell 138 in the region R is the inner surface including the region R in the direction of the axial line O.

In the present invention, the tensile strength of the material of the protector 140 according to JIS-G0567 at 800 degrees Celsius may be greater than that of the material of the metal shell 138. In such a case, the heat resistance of the protector 140, which is positioned outermost at the front end of the gas sensor 200, is further increased. As a result, the heat resistance of the gas sensor 200 can be further increased.

The present invention is not limited to the above-described embodiment, and it goes without saying that the present invention includes various modifications and equivalents within the spirit and scope of the present invention.

The shapes and other characteristics of the protector and the metal shell to which the protector is joined are not limited to those described above. For example, although the protector has a two-element structure including the inner protector element and the outer protector element in the above-described embodiment, the protector may instead have a single-element structure.

The protector and the metal shell are preferably, but necessarily, joined together by welding.

The gas sensor is not limited to an oxygen sensor or a universal gas sensor, and may instead be, for example, a NOx sensor. The sensing element may be tubular.

The strength of the material of the metal shell is preferably greater than that of the material of the protector.

Gas sensors 200 having the structure illustrated in FIG. 1 were manufactured. In each gas sensor 200, the protector 140 was made of an austenitic stainless steel to which Nb was added, and the metal shell 138 was made of SUS430LX according to JIS. The ratio (t1/t2) was set to different values. The protector 140 was fixed to the outer surface of the front end portion 138s of the metal shell 138 by all around welding.

These gas sensors 200 were subjected to 500 heating-cooling cycles, in each of which the temperature was set to 900 degrees Celsius for 20 minutes and then to 200 degrees Celsius for 20 minutes. Then, the joined portion W of each gas sensor 200 was visually evaluated for breakage and deformation, and graded as follows:

GOOD: No separation of the back-end coupled portion 140b of the protector 140 from the joined portion W or deformation of the metal shell 138 was found.

BAD: Separation of the back-end coupled portion 140b or deformation of the metal shell 138 was found.

The results are shown in FIG. 4.

FIG. 4 shows that, when 0.6≤(t1/t2)≤2.0 was satisfied, no separation of the back-end coupled portion 140b of the protector 140 from the joined portion W or deformation of the metal shell 138 occurred. Thus, breakage or other damage to the joined portion W did not occur.

When (t1/t2)<0.6, separation of the back-end coupled portion 140b of the protector 140 from the joined portion W occurred. When (t1/t2)>2.0, deformation of the metal shell 138 occurred.

What is claimed is:

1. A gas sensor comprising:
    a sensing element that extends in an axial line direction, the sensing element including a detecting portion at a front end of the sensing element;
    a metal shell that is tubular, the metal shell surrounding the sensing element such that the detecting portion projects from a front end of the metal shell; and
    a protector made of metal, the protector fixed to the metal shell and containing the detecting portion,
    wherein a coefficient of thermal expansion of a material of the protector at 800 degrees Celsius is higher than a coefficient of thermal expansion of a material of the metal shell at 800 degrees Celsius,
    wherein a back end portion of the protector is joined to an outer surface of the metal shell to form a joined portion having a cross section in which a minimum distance t1 between the outer surface of the metal shell and an outer surface of the protector and a minimum distance t2 between the outer surface of the metal shell and an inner surface of the metal shell satisfy $0.6 \leq (t1/t2) \leq 2.0$, and
    wherein a part of the detecting portion of the sensing element is surrounded by the inner surface of the metal shell.

2. The gas sensor according to claim 1,
    wherein the protector includes
        an inner protector element arranged such that a gap is defined between the inner protector element and the detecting portion, and
        an outer protector element arranged such that a gap is defined between the outer protector element and the inner protector element, and
    wherein the joined portion is formed on a back-end coupled portion in which a back end portion of the inner protector element and a back end portion of the outer protector element overlap.

3. The gas sensor according to claim 1, wherein the metal shell includes a first inner surface in a region obtained by projecting the joined portion on the outer surface of the metal shell onto the inner surface of the metal shell and a back inner surface connected to a back end of the first inner surface, the first inner surface being radially outside the back inner surface.

4. The gas sensor according to claim 1, wherein a tensile strength of the material of the protector according to JIS-G0567 at 800 degrees Celsius is greater than a tensile strength of the material of the metal shell according to JIS-G0567 at 800 degrees Celsius.

5. The gas sensor according to claim 1, wherein the material of the protector is an austenitic stainless steel and the material of the metal shell is a ferritic stainless steel.

* * * * *